United States Patent [19]

Berlin

[11] 4,106,508
[45] Aug. 15, 1978

[54] CLAMP DEVICE

[76] Inventor: Richard Barnard Berlin, 309 Engle St., Englewood, N.J. 07631

[21] Appl. No.: 719,283

[22] Filed: Aug. 31, 1976

[51] Int. Cl.$^2$ ............................................. A61B 17/12
[52] U.S. Cl. .................................. 128/346; 128/325; 251/7
[58] Field of Search .................... 24/115 G, 16 R, 19; 81/3.8, 9.3; 128/346, 325, 326; 251/7

[56] References Cited

U.S. PATENT DOCUMENTS

| | | | |
|---|---|---|---|
| 1,840,150 | 1/1932 | Bodendieck | 81/3.8 |
| 2,215,725 | 9/1940 | Martinson | 128/346 X |
| 2,678,000 | 5/1954 | Scheidt et al. | 81/3.8 X |
| 3,147,754 | 9/1964 | Koessler | 128/346 |
| 3,182,373 | 5/1965 | Strand | 128/346 UX |
| 3,993,076 | 11/1976 | Fogarty | 128/325 |

FOREIGN PATENT DOCUMENTS 361,792 2/1973 U.S.S.R. .................................. 128/346

OTHER PUBLICATIONS

Wylie, "A New Aorta Clamp", in Surgery 36$^4$: 781–783, 1954.
Langston, "Valvulotomy for Pulmonary Stenosis . . . ", in Int. Abstr. of Surgery, 97$^6$: 549–550, 1953.

Primary Examiner—Robert W. Michell
Assistant Examiner—Michael H. Thaler
Attorney, Agent, or Firm—Depaoli & O'Brien

[57] ABSTRACT

This invention provides a clamp device which is suitable for medical applications. The device is adapted for use as a surgical clamp for the occlusion of blood vessels or other tubular conduits in human and other animal bodies.

7 Claims, 9 Drawing Figures

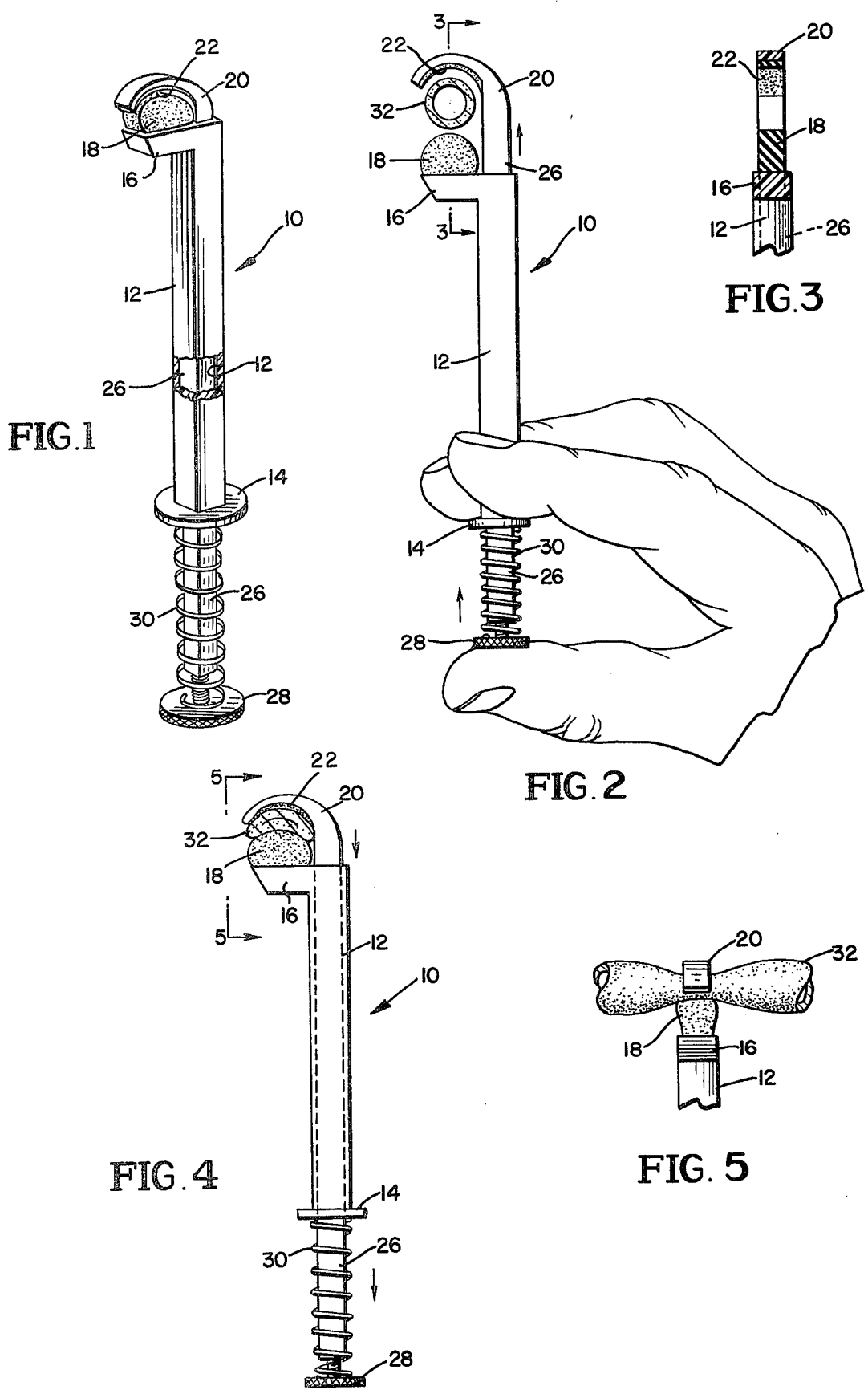

CLAMP DEVICE

BACKGROUND OF THE INVENTION

There remains a need for clamp devices adapted for surgical procedures which can occlude a tubular conduit, such as an artery, vein, or intestine, with little or no damage to fragile tissue.

In order to perform surgery upon blood vessels, particularly arteries which are under high pressure, it is often necessary to create a temporary barrier to the flow of blood through the tubular conduit. Various metal and plastic devices are known and used to perform this function. In most cases, the devices depend upon compressive force and hard gripping surfaces to prevent slippage. The force required to occlude a blood vessel is usually sufficiently concentrated to damage the walls of the blood vessel. The blood vessels most commonly operated upon are those which are diseased and degenerated. Such blood vessels are susceptible to damage by compressive forces, and thereby increase the prospect of surgical complications.

Typical of the surgical clamping instruments known in the medical field are those described in U.S. Pat. Nos. 2,686,521; 2,796,867; 3,171,184; 3,363,628; 3,461,876; 3,503,396; 3,503,398; 3,507,270; 3,509,882; 3,538,917; 3,581,551; 3,730,186; 3,766,925; 3,786,816; 3,797,489; 3,840,018; and references cited therein.

While each of the known surgical clamps has advantages for specific surgical procedures, none have been found to provide design features which are ideally suited for occlusion of blood vessels which are in a diseased or degenerated condition.

Some surgical clamps have hard gripping surfaces which occlude tubular conduits by squeezing the lumen space flat. Other surgical clamps are large metal devices which are difficult to introduce into constricted body cavities, or cannot be quickly applied or removed as may be necessary. Still other surgical clamps are complex in design, expensive, and difficult to clean and sterilize for reuse.

Accordingly, it is an object of the present invention to provide a clamp device adapted for occluding a tubular conduit such as an artery, vein, or intestine.

It is another object of the present invention to provide a surgical clamp which can occlude a blood vessel with an adjustable compressive force.

It is another object of the present invention to provide a surgical occluder for blood vessels which can be applied and removed rapidly with single hand manipulation.

It is a further object of the present invention to provide a surgical occluder which has a firmly flexible and pressure-deformable clamping grip which minimizes damage to tubular conduits in a fragile condition.

Other objects and advantages shall become apparent from the accompanying description and drawings.

SUMMARY OF THE INVENTION

One or more objects of the present invention are accomplished by the provision of a clamp device adapted for occluding flexible tubular conduits comprising (1) a first jaw member having a hook configuration with a concave inner surface; (2) a second jaw member having a resiliently deformable convex inner surface; (3) a coextensive connecting means for moving and guiding said jaw members in an oppositely disposed and linearly engageable relationship; and (4) a biasing means for urging said jaw members into contacting and inner surface conforming proximity.

BRIEF DESCRIPTION OF THE DRAWINGS

FIG. 1 is a perspective view of a preferred surgical clamp design with a portion broken away to illustrate a square shaft and housing design which eliminates misalignment or torque movement of the linearly engageable jaw members;

FIG. 2 is a side elevation view of the same surgical clamp design being hand operated for application to a flexible tubular conduit;

FIG. 3 is a cross-sectional view taken along line 3—3 of FIG. 2 with flexible tubular conduit not shown;

FIG. 4 is a side elevation view of FIG. 2 after adjustment for pressure and release of spring-controlled first jaw member shaft extension; and FIG. 5 is a fragmentary front elevation of FIG. 4 to illustrate the occlusion of the lumen of a flexible tubular conduit such as an artery, vein or intestine.

DETAILED DESCRIPTION OF INVENTION EMBODIMENTS

Figure 6:
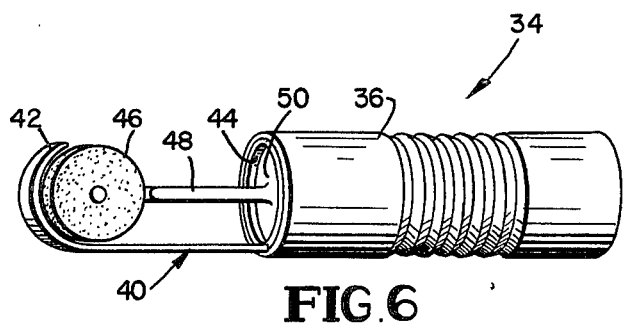
FIG. 6 is an isometric side view of an elastomeric spring biased surgical clamp embodiment in a closed jaw position.

A present invention clamp device can vary in length dimension over a range between about 3 and 30 centimeters. The width dimension of the jaw members can vary over a range between about 0.1 and 3 centimeters. The width of the two jaw members can be of different dimensions, respectively.

The present invention clamp device can be fabricated with either metal or plastic structural components, which can be disassembled easily for cleaning and sterilizing. Low cost disposable clamp devices are contemplated as an embodiment of the present invention, e.g., surgical clamps produced with low cost plastic or cellulosic components.

In FIG. 1, a clamp device 10 is illustrated which is specially adapted for occluding a tubular conduit in an animal body. Illustrative of such conduits are the aorta, iliac, femoral and carotid arteries, the jugular vein, and the small and large intestines.

Clamp device 10 as represented has an extended shaft housing 12 which has a finger grip configuration 14 at the lower extremity of shaft housing 12. The housing 12 functions as a handle for manipulation of the clamp device. Housing 12 has an extension base 16 at its upper extremity, which supports an attached resiliently deformable plunger 18.

The plunger 18 is shaped to contact and conform to the inner surface 22 of a hook-shaped jaw 20. The hook-shaped jaw 20 has an extended shaft 26 which is slidably disposed and guided in shaft housing 12. Shaft 26 is maintained under bias tension by coil spring 30. The coil spring applied force is regulated by screw 28 which is set in the end of shaft 26.

In FIG. 2, a flexible tubular conduit 32 is illustrated in juxtaposition between plunger 18 and inner jaw surface 22. Inner surface 22 can be the smooth face of the jaw 20 structure, e.g., metal or firm plastic such as polypropylene or polycarbonate. The inner surface 22 can also be a lining insert which is a resiliently deformable elastomeric or textile material. Both housing 12 and shaft 26 can be in a curved configuration to facilitate palming for one-handed manipulation.

Figure 7:
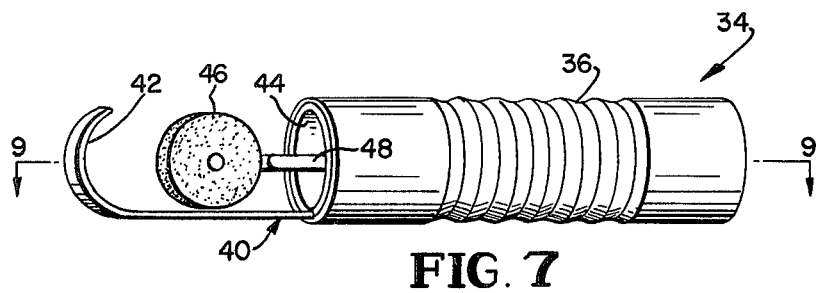
FIG. 7 is an isometric view of the FIG. 6 surgical clamp with the elastomeric accordian-sleeve spring and the second jaw member pulled back to separate the two jaw members.
Figure 8:
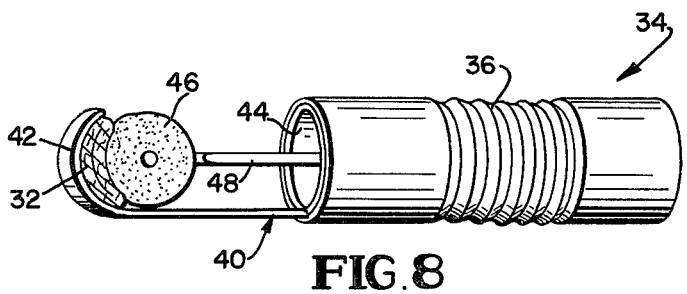
FIG. 8 is an isometric view of the FIG. 6 surgical clamp with a flexible tubular condiut occluded between the jaws under elastomeric spring-applied pressure.
Figure 9:
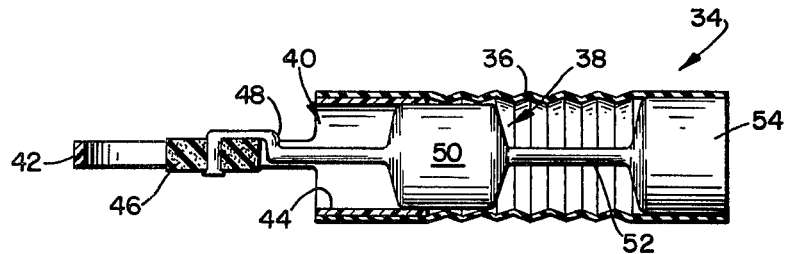
FIG. 9 is a cross-sectional view taken along line 9—9 of FIG. 7 with the enclosed second jaw shaft extension in full lines to illustrate the shape and positioning of one type of shaft extension design.

An alternative clamp device design is represented in FIG. 6 through FIG. 9. The clamp device 34 has an elastomeric accordian sleeve 36 which encloses plunger assembly 38. Hook-shaped jaw 42 is attached to plunger guide assembly 44 by extended shaft 40.

Resiliently deformable plunger 46 is attached to support shaft 48, which in turn is integrally attached to piston body 50. The piston body 50 is connected to fixed end base 54 by shaft 52.

A clamp device of the present invention can occlude a blood vessel with sufficient force to obstruct the flow of blood. The hook-shaped first jaw prevents the possibility of the clamp device slipping off the blood vessel. The configuration of the two jaws permits occlusion to be accomplished with less pressure on the blood vessel, and consequently less trauma. In addition, blood vessels frequently contain calcified plaques which are brittle and which fragment under sharp pressure with undesirable effects. The jaw configuration in a present invention surgical clamp can cradle plaques and thereby minimize the likelihood of fragmentation and embolization or clotting.

What is claimed is:

1. A clamp device adapted for occluding flexible tubular conduits comprising (1) a hook-shaped first jaw member with a concave inner surface, which jaw member is attached to an extended shaft, said first jaw member together with said shaft forming the shape of a J; (2) a second jaw member with a resiliently deformable convex inner surface, which jaw member is attached to an extended shaft, wherein said extended shafts are coextensively and slidably connected for moving and guiding said jaw members to maintain the concave and convex inner surfaces of said jaw members in an oppositely disposed and longitudinally engageable contacting relationship; and (3) biasing means for urging said jaw members into concave and convex inner surface contacting and conforming proximity.

2. A clamp device in accordance with claim 1 wherein the biasing means is adapted to apply a selectively adjustable urging force.

3. A clamp device in accordance with claim 1 wherein the biasing means is a coil spring.

4. A clamp device in accordance with claim 1 wherein the biasing means is an elastomeric spring.

5. A clamp device in accordance with claim 1 wherein the biasing means has a threaded screw adjustment.

6. A clamp device in accordance with claim 1 wherein the resiliently deformable convex inner surface of said second jaw member is composed of elastomeric material.

7. A clamp device in accordance with claim 1 wherein the concave inner surface of said hook-shaped first jaw member is resiliently deformable.

* * * * *